(12) United States Patent
Marino et al.

(10) Patent No.: US 6,913,614 B2
(45) Date of Patent: Jul. 5, 2005

(54) DELIVERY SYSTEM WITH SAFETY TETHER

(75) Inventors: Joseph A. Marino, Apple Valley, MN (US); Michael P. Corcoran, Oakdale, MN (US)

(73) Assignee: Cardia, Inc., Burnsville, MN (US)

( * ) Notice: Subject to any disclaimer, the term of this patent is extended or adjusted under 35 U.S.C. 154(b) by 48 days.

(21) Appl. No.: 10/431,717

(22) Filed: May 8, 2003

(65) Prior Publication Data

US 2004/0225324 A1 Nov. 11, 2004

(51) Int. Cl.⁷ .............................................. A61B 17/08
(52) U.S. Cl. ...................................................... 606/213
(58) Field of Search .................. 606/213, 200

(56) References Cited

U.S. PATENT DOCUMENTS

| | | | |
|---|---|---|---|
| 3,874,388 A | 4/1975 | King et al. | 128/334 |
| 4,007,743 A | 2/1977 | Blake | 128/334 |
| 4,917,089 A | 4/1990 | Sideris | 606/215 |
| 5,108,420 A | 4/1992 | Marks | 606/213 |
| 5,171,259 A | 12/1992 | Inoue | 606/213 |
| 5,284,488 A | 2/1994 | Sideris | 606/213 |
| 5,334,137 A | 8/1994 | Freeman | 604/8 |
| 5,334,217 A | 8/1994 | Das | 606/213 |
| 5,382,260 A | 1/1995 | Dormandy, Jr. et al. | 606/151 |
| 5,397,331 A | 3/1995 | Himpens et al. | 606/151 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,634,936 A | 6/1997 | Linden et al. | 606/213 |
| 5,649,950 A | 7/1997 | Bourne et al. | 606/194 |
| 5,702,421 A | 12/1997 | Schneidt | 606/213 |
| 5,709,707 A | 1/1998 | Lock et al. | 606/213 |
| 5,725,552 A | 3/1998 | Kotula et al. | 606/213 |
| 5,741,297 A | 4/1998 | Simon | 606/213 |
| 5,776,079 A | 7/1998 | Cope et al. | |
| 5,904,703 A | 5/1999 | Gilson | 606/213 |
| 6,024,756 A | 2/2000 | Huebsch et al. | 606/213 |
| 6,174,322 B1 * | 1/2001 | Schneidt | 606/213 |
| 6,206,907 B1 | 3/2001 | Marino et al. | 606/215 |
| 6,379,368 B1 | 4/2002 | Corcoran et al. | 606/153 |

FOREIGN PATENT DOCUMENTS

| | | |
|---|---|---|
| DE | 233 303 | 2/1986 |
| DE | 42 22 291 C1 | 1/1994 |
| EP | 0 362 113 | 4/1993 |
| EP | 0 541 063 | 9/1998 |
| GB | 2 269 321 A | 9/1994 |
| GB | 2269321 | 9/1994 |

\* cited by examiner

*Primary Examiner*—Vy Bui
(74) *Attorney, Agent, or Firm*—Kinney & Lange, P.A.

(57) ABSTRACT

A delivery system that allows a physician to deploy a medical device and refract both the catheter and delivery device while keeping the device connected to a safety tether. The tether is thin and extremely flexible, so it does not distort the tissue. The tether allows the physician to observe the placement of the medical device without having fully released the medical device and without tissue contortion caused by the stiffer catheter and delivery device. In addition, the device is easily retrievable if it is not positioned properly because it has not been fully released. This system also comprises a coupler which connects the medical device to the delivery device.

16 Claims, 6 Drawing Sheets

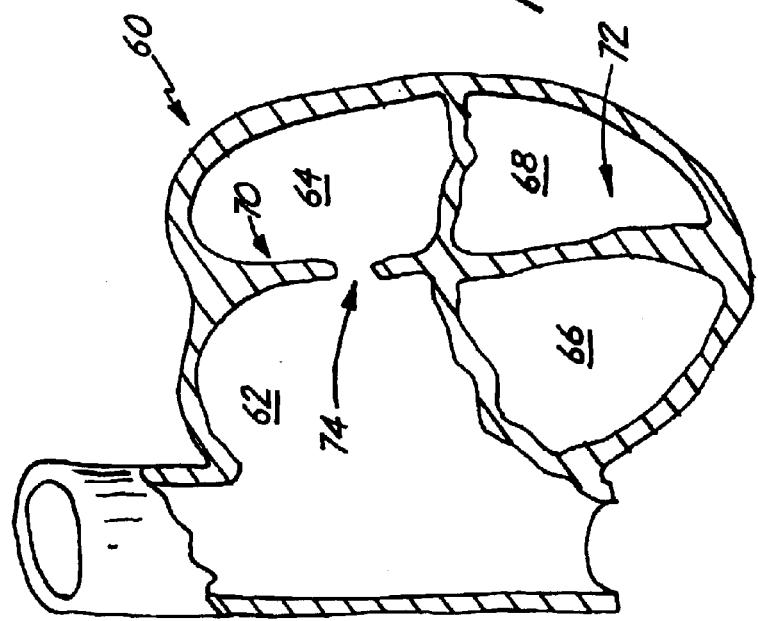
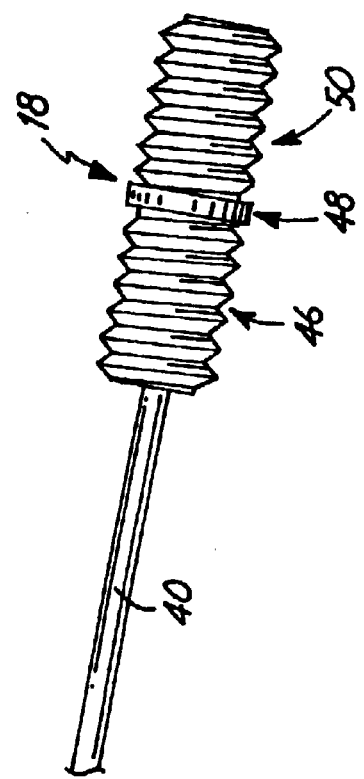
Fig. 4
Fig. 3

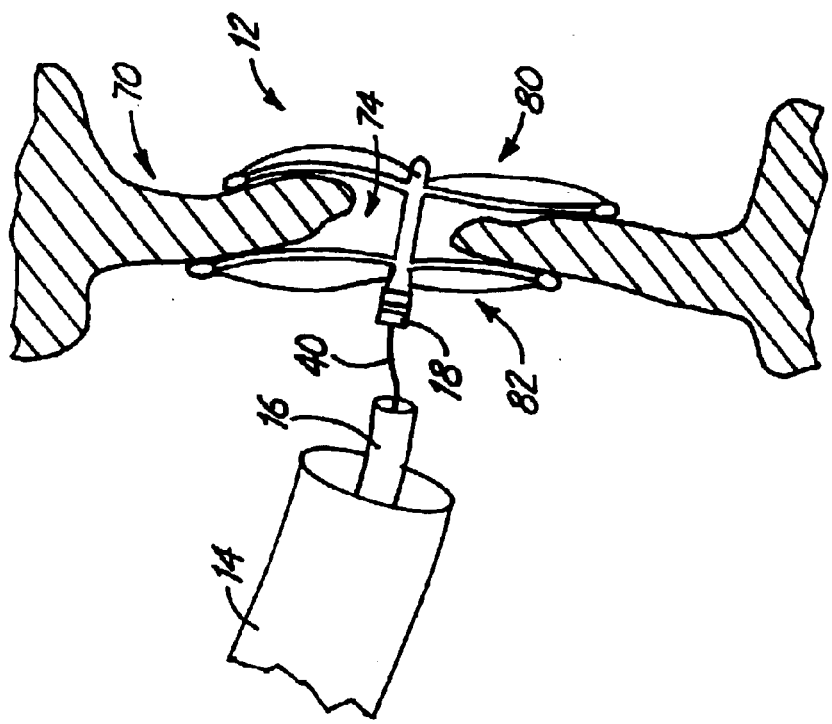
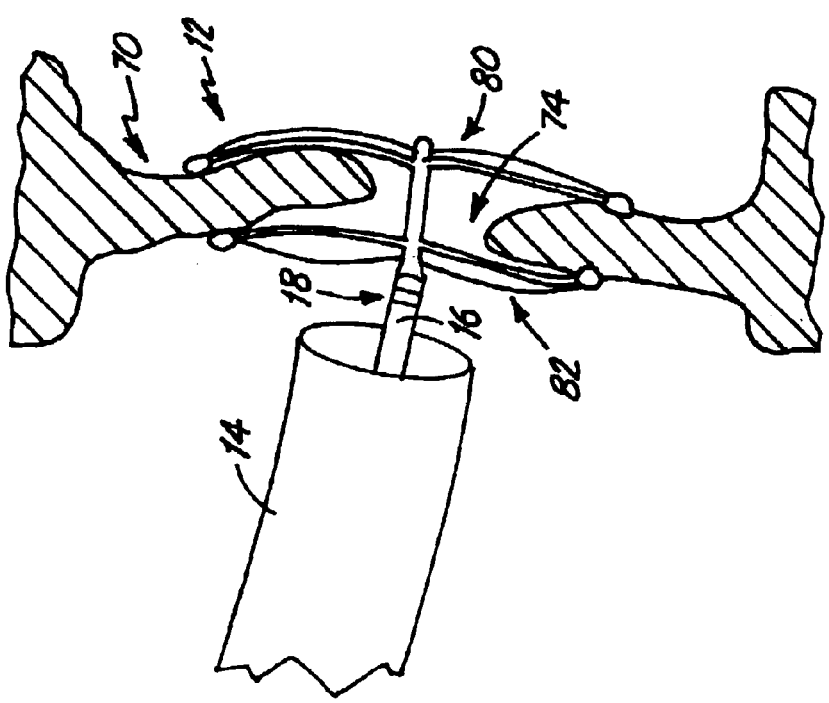

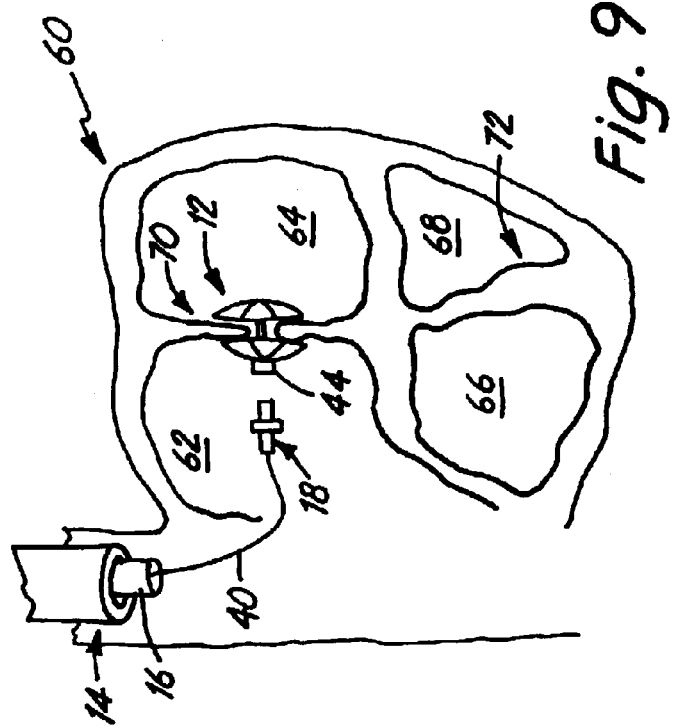
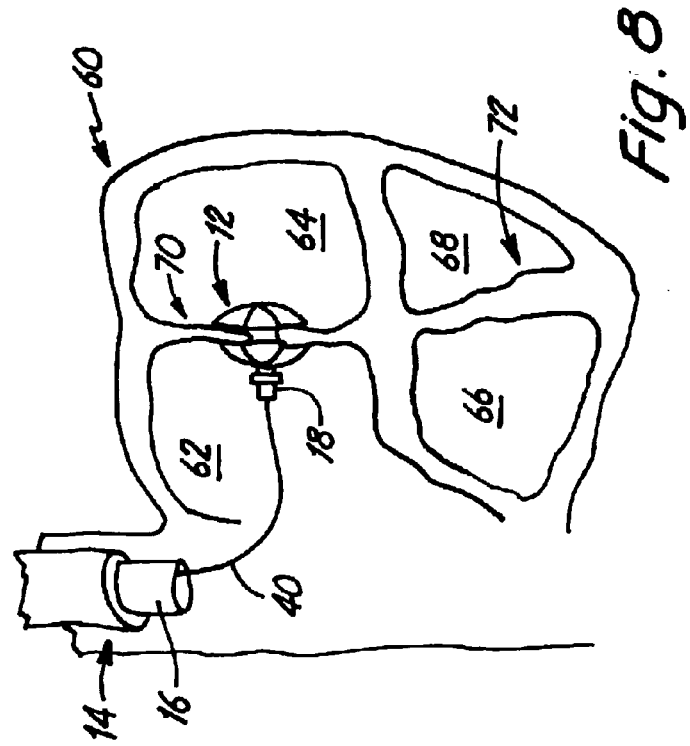

DELIVERY SYSTEM WITH SAFETY TETHER

CROSS-REFERENCE TO RELATED APPLICATION(S)

None.

BACKGROUND OF THE INVENTION

This invention relates to a percutaneous transcatheter delivery system for a medical device, particularly an occlusion device, which allows a physician to deliver the device and observe its position without the tissue contortion caused by a stiff catheter or delivery device while the device remains tethered to the system.

Current medical technology provides for the percutaneous implantation of medical devices, delivered through a catheter, which gives individuals an option to traditional surgery in a variety of medical situations.

Generally this procedure begins by inserting a guidewire into a major blood vessel and advancing it through the body to the treatment location. Next, a catheter is advanced over the guidewire until it reaches the treatment location, so that the guidewire can then be removed. A medical device is then attached to a delivery device (also called a delivery forceps) which is used to advance the medical device through the catheter to the treatment location. Once the medical device is properly positioned it is released from the delivery device.

For example, permanently repairing cardiac apertures in adults and children normally requires open heart surgery which is a risky, expensive, and painful procedure. To avoid the risks and discomfort associated with open heart surgery, modern occlusion devices have been developed that are small, implantable devices capable of being delivered to the heart through a catheter to occlude the aperture. This procedure is performed in a cardiac cathlab and avoids the risks and pain associated with open heart surgery.

To deliver an occlusion device, a guidewire and a catheter are inserted into a major blood vessel and advanced, through the body, to the treatment site. To allow for proper control and maneuvering, each item of the delivery system, including the guidewire, catheter, and delivery device, must be sufficiently stiff to maneuver to the desired location despite resistance caused by contact with the surface of the vasculature and turns in the body. At the same time, guidewires, catheters, and delivery devices must also be flexible enough to navigate the numerous turns in the body's vasculature. The necessary stiffness of the guidewire, catheter, and delivery device may distort the tissue on the way to and at the site of the defect, making it difficult to optimally position the occlusion device.

One difficulty in implanting occlusion devices is ensuring that the occluder conforms to the contours of the defect. Poor conformation to the defect results in poor seating of the occlusion device which decreases the ability of the occlusion device to occlude the defect. Ensuring the proper seating of an occlusion device once it has been deployed poses a continuing challenge given the uneven topography of the vascular and septal walls of each patient's heart. The challenge in correctly positioning an occluder so that it conforms to the uneven topography is compounded by the fact that the contours of each defect in each individual patient are unique.

Distortion of tissue surrounding the defect caused by the stiffness of the guidewire, catheter, or delivery device adds to the seating challenge. If the surrounding tissue is distorted by the catheter, it is difficult to determine whether the occlusion device will be properly seated once the catheter is removed and the tissue returns to its normal state. If the occlusion device is not seated properly, it may have to be retrieved and re-deployed. Both doctors and patients prefer to avoid retrieval and re-deployment because it causes additional expense and longer procedure time. Worse yet, if the occlusion device embolizes or is improperly deployed, retrieval of the device may require open heart surgery.

Releasing the occlusion device from the delivery device also poses challenges to treatment. Currently, a variety of release mechanisms are used to release an occlusion device from the delivery device. Some release mechanisms work by pulling or twisting a handle of the delivery device in order to release the occlusion device. This pulling on or twisting of the delivery device may make the delivery device very stiff due to the tension created by the release mechanism. The tension may add to tissue contortion.

One example of a current release system is a delivery device with a small jaw on the end which grasps the occlusion device. The small jaw is connected to a long wire. Pulling on the wire opens the jaw and releases the occlusion device. A drawback to this design is the tension that is created when the wire is pulled. When the wire must be pulled to release the occlusion device, the delivery device becomes very stiff, particularly at the end of the device closest to the occlusion device. This stiffness near the occlusion device distorts the tissue at the location where the occlusion device is to be deployed. As a result, it is difficult to judge whether or not the occlusion device is properly placed, or whether or not it will remain properly placed once released from the device and the tissue returns to normal.

Thus, there is a need in the art for a delivery system that allows physicians to observe the placement of an internal medical device without tissue contortion that also allows for easy release and retrieval.

BRIEF SUMMARY OF THE INVENTION

The present invention is a delivery system that allows a physician to deploy a medical device and retract both the catheter and delivery device, leaving only the medical device and a tether. The tether is thin and extremely flexible, so it does not distort the surrounding tissue. The tether system allows a physician to determine whether the device is properly positioned prior to releasing the device. If the device has been successfully deployed, and the physician is satisfied with the placement of the device, the tether is removed. If not, the device is easily retrievable using the tether. Because the device is still attached to the tether, the catheter can be repositioned near the device, and using the tether, the medical device can with drawn back into the catheter.

This delivery system may further comprise a coupler for connecting the device to the tether. The tether is permanently affixed to the proximal end of the coupler. Thus, the tether is able to connect to both the medical device and the delivery device via the coupler. One embodiment of the coupler has threading on both ends so that it can be screwed into or unscrewed from both the delivery device and the medical device.

BRIEF DESCRIPTION OF THE DRAWINGS

FIG. 3 is a side perspective view of a coupler having threading on each end, fixed to a tether.

FIG. 4 is a diagram of the human heart with a septal defect.

FIG. 6 is an illustration of an occlusion device deployed in the heart.

FIG. 7 is an illustration of the heart with an occlusion device having both sides deployed, the catheter and delivery device partially withdrawn, and a tether connected to the occlusion device.

FIG. 8 is an illustration of the heart with an occlusion device having both sides deployed, the catheter and delivery device partially withdrawn, and a tether connected to the occlusion device FIG. 9 is an illustration of the heart with an occlusion device having both sides deployed, the catheter and delivery device partially withdrawn, and the tether disconnected from the occlusion device.

DETAILED DESCRIPTION

Figure 1:
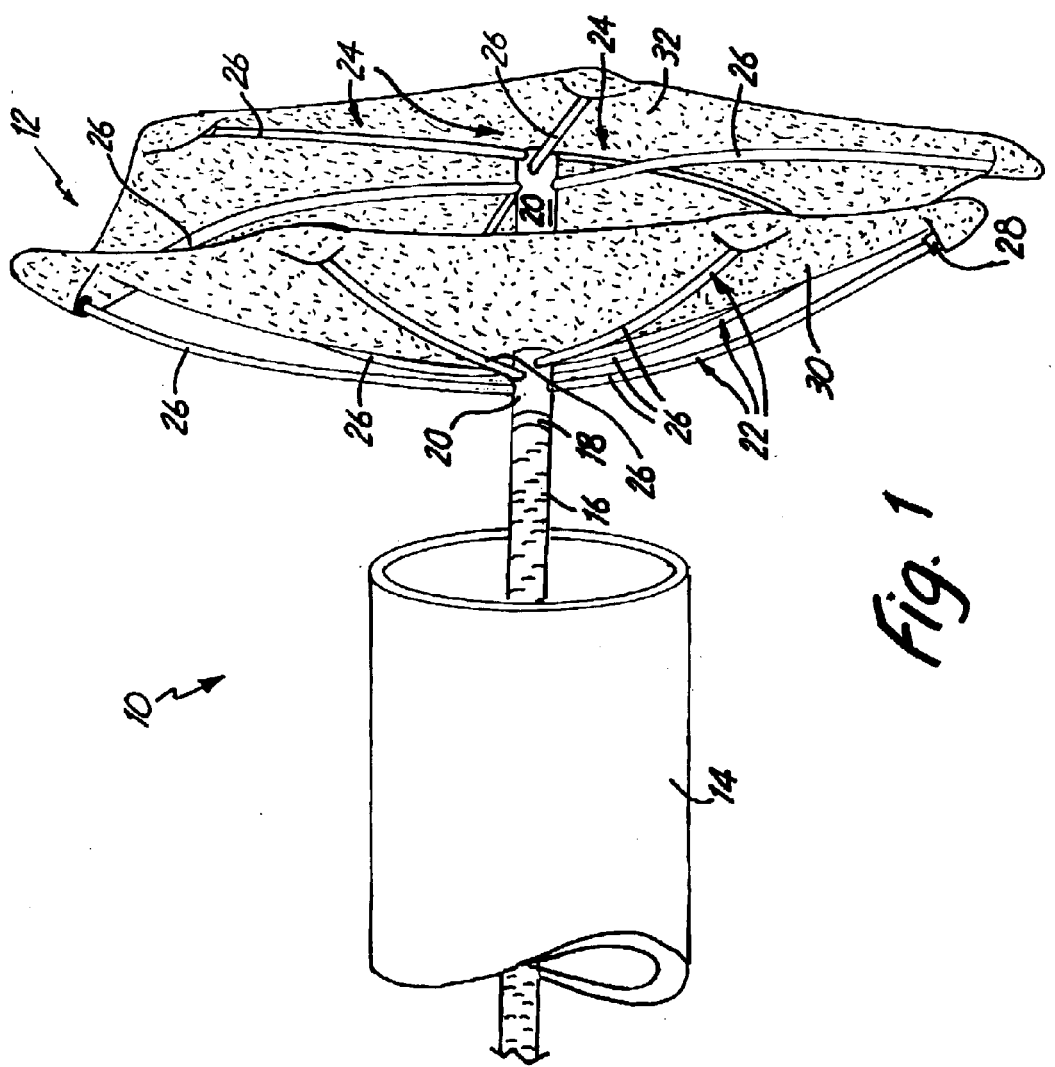
FIG. 1 is a side perspective view of delivery system with an occlusion device attached.

FIG. 1 is a side perspective view of a delivery system 10 for a medical device with an occlusion device 12 attached. As viewed from left to right in FIG. 1, the delivery system 10 comprises a catheter 14, a hollow delivery device 16, a coupler 18, and an occlusion device 12. The delivery device 16 passes through the catheter 14 and attaches to the coupler 18. The coupler 18 attaches to both the occlusion device 12 and the delivery device 16, joining them together. The coupler 18 may be released from either the occlusion device 12 or the delivery device 16 while remaining attached to the other. The occlusion device 12 comprises a center section 20, proximal and distal fixation devices 22, 24 (each comprised of six arms 26), atraumatic tips 28, a proximal sheet 30, and a distal sheet 32.

As viewed in FIG. 1, the proximal and distal fixation devices 22, 24 are connected to the center section 20. One method of connecting the arms 26 to the center 20 is to provide the center section 20 with drill holes through which the arms 26 extend. The sheets 30, 32 may be attached to the proximal and distal fixation devices 22, 24 using sutures or other suitable methods. In this way, the sheets 30, 32 may be sewn to the fixation devices 22, 24 at the atraumatic tips 28. The atraumatic tips 28, located at the distal end of each arm 26 and serve to minimize damage to the surrounding tissue.

The occlusion device 12 is constructed so that the proximal and distal fixation devices 22, 24 are easily collapsible about the center section 20. Due to this construction, the occlusion device 12 can be folded so that the fixation devices 22, 24 are folded in the axial direction, which allows the device 12 to be deployed using a catheter. The proximal and distal sheets 30, 32 attached to the proximal and distal fixation devices 22, 24 are flexible, and can likewise collapse as the proximal and distal devices 22, 24 are folded.

Once the device 12 is deployed, the fixation devices 22, 24 serve to hold the proximal and distal sheets 30, 32 in place to seal a defect. To ensure there is sufficient tension to hold the sheets 30, 32 in place, the fixation devices 22, 24 may be made of a material capable of shape memory, such as a nickel-titanium alloy, commonly called Nitinol. Nitinol is preferably used because it is commercially available, very elastic, non-corrosive, and has a fatigue life greater than that of stainless steel. To further ensure that the fixation devices 22, 24 do not suffer from fatigue failures, one embodiment of the present invention relies on making the wire fixation devices 22, 24 of stranded wire or cables.

Figure 2:
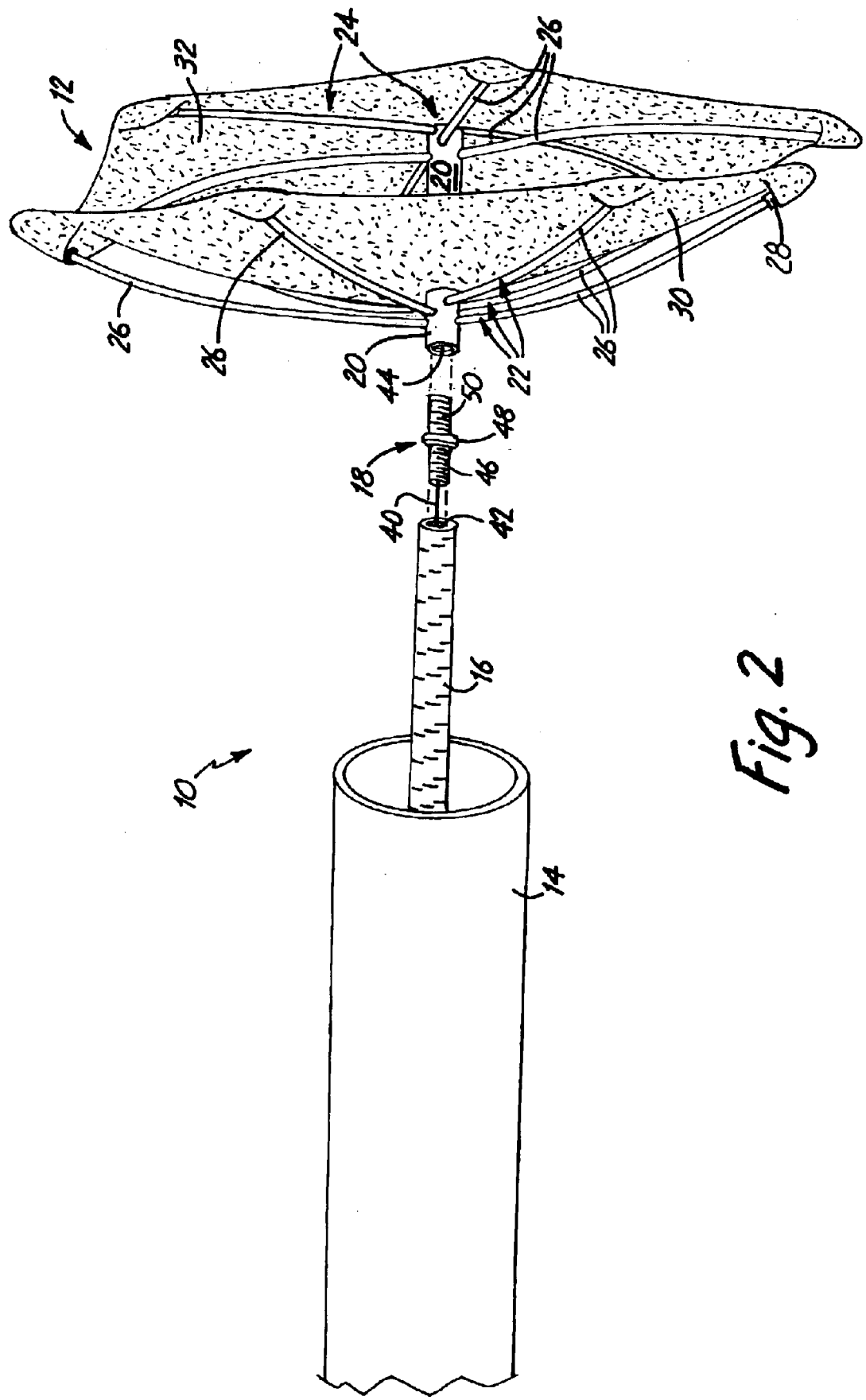
FIG. 2 is an exploded side perspective view of a delivery system with an occlusion device.

FIG. 2 is an exploded side view of the delivery system 10 illustrating the manner in which a tether 40 can be used with the occlusion device 12. Viewed from left to right is the delivery system 10, the catheter 14, the hollow delivery device 16, a tether 40, the coupler 18, and the occlusion device 12. The distal end of the delivery device 16 has threading on the distal end lumen 42. Again, the occlusion device 12 has proximal and distal fixation devices 22, 24 (each comprised of six arms 26), atraumatic tips 28, the proximal sheet 30, and the distal sheet 32. In this embodiment of the device 12 the center section 20 has a threaded lumen 44. The coupler 18 has a first threaded side 46, a center 48, and a second threaded side 50.

The double threaded coupler 18 is one way to attach the tether 40 to the device 12. In this embodiment, the tether 40 is permanently fixed to the coupler 18 which is threaded the first side 46 and the second side 50. The center section 20 of the occlusion device 12 also has a threaded female lumen 44 where the coupler 18 attaches to the occlusion device 12. Likewise, the distal end of the delivery device 16 has threading on the distal end lumen 42 where the coupler 18 attaches to the delivery device 16. Thus, the delivery device 16 may be unscrewed from the coupler 18 and retracted, leaving only the occlusion device 12, the coupler 18, and the tether 40.

The tether 40 is preferably constructed of Nitonol wire but may also be stainless steel, titanium or polymer. The diameter of the tether 40 is small enough to assure that the tether 40 is highly flexible. As mentioned above, the tether 40 is flexible and so that it does not distort tissue. The tether 40 may be tapered or of variable diameter. When made to have a variable diameter, the tether 40 may be small and flexible at the distal end, but may be wider at the proximal end to ensure that it is graspable and maneuverable.

FIG. 3 is a side perspective view showing the coupler 18 in greater detail. The coupler 18 is threaded on both the first side 46 and the second side 50. The two sides 46, 50 are separated by a center 48. Also shown is the tether 40 which is permanently fixed to the coupler 18. For additional safety, the sides 46, 50 of the coupler 18 may be threaded in reverse directions to minimize the chance of accidental release. However, the tether 40 and thus, the coupler 18, can be held stationary by hand, while a delivery device is rotated to release the coupler 18 from a delivery device so reverse threading is not a necessary feature.

FIG. 4 is a diagrammatic view of a human heart 60. Visible in FIG. 4 is right atrium 62, left atrium 64, right ventricle 66, left ventricle 68. The right atrium 62 is separated from the left atrium 64 by an atrial septal wall 70. The right ventricle 66 is separated from the left ventricle 68 by a ventricular septal wall 72. Also visible in FIG. 4 is an atrial septal defect 74 located in the atrial septal wall 70, between the right atrium 62 and left atrium 64 of the heart 60. An atrial septal defect 74 is one example of a cardiac defect that may be occluded using an occlusion device.

Figure 5:
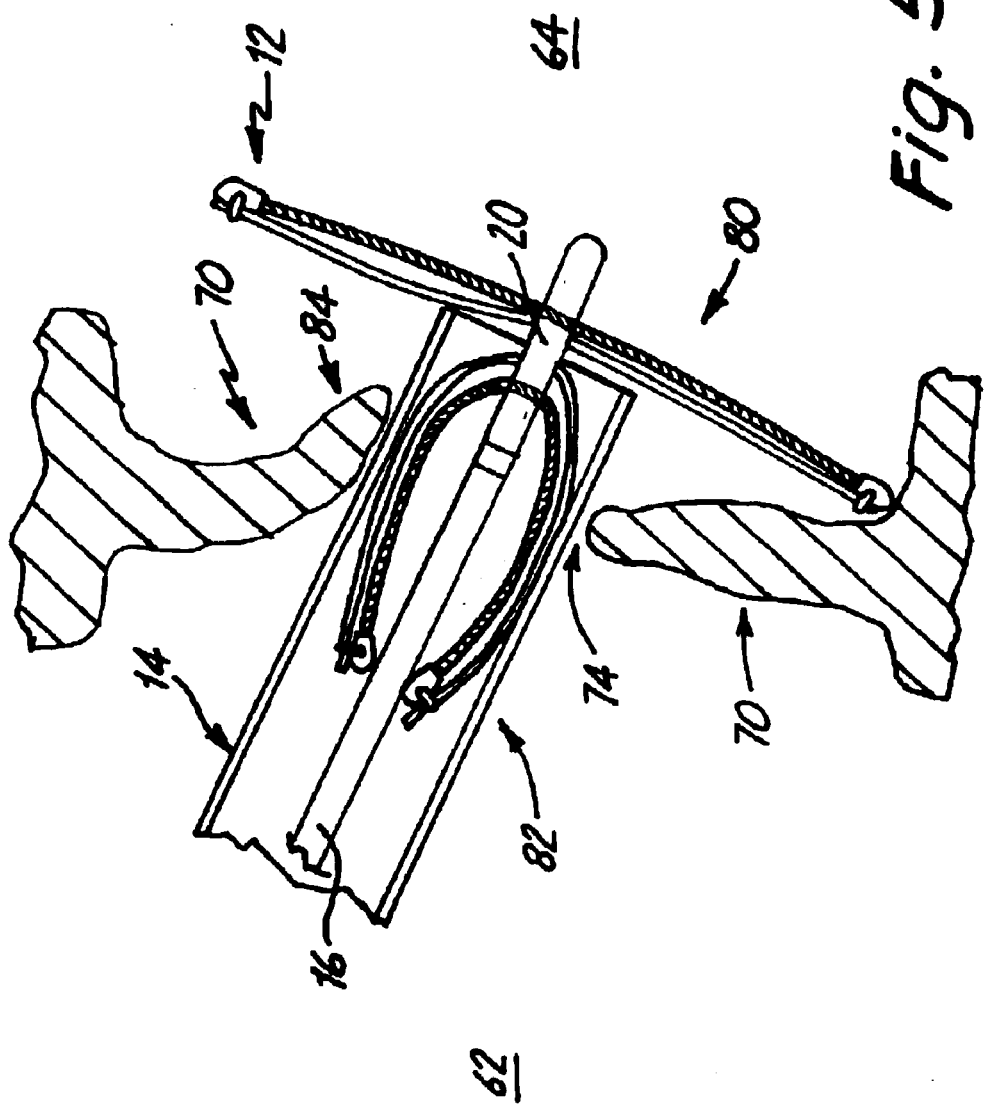
FIG. 5 shows an occlusion device having one side deployed into a heart with a septal defect.

FIGS. 5 through 9 illustrate the method by which an occlusion device 12 is deployed using the present invention. FIG. 5 is a more detailed view of the septal wall 70 and the defect 74 shown between the right atrium 62 and the left atrium 64. Also shown is the occlusion device 12 of FIG. 1, a catheter 14, and a delivery device 16. As viewed in FIG. 5, the occlusion device 12 comprises a distal side 80, a proximal side 82, and the center section 20. The occlusion device 12 has been loaded into the catheter 14 and is attached to the delivery device 16. The occlusion device 12 has been advanced through the catheter 14 to the location of the defect 74 using the delivery device 16.

To deploy the occlusion device 12 at the defect 74, the catheter 14 is positioned past the septal defect 74. Once the catheter 14 is properly positioned, the delivery device 16 is used to push the occlusion device 12 out of the catheter 14. The delivery device 16 is used first to push the occlusion device 12 through the catheter 14 so that only the distal side 80 of the device 12 is exposed in the left atrium 64. After exiting the catheter, the distal side 80 of the device 12 expands against septal wall 70 surrounding the defect 74. Although the distal side 80 has been deployed, the proximal side 82 is still folded in the catheter 14.

The proximal side 82 of the device 12 can be deployed in a similar manner. To deploy the proximal side 82, the catheter 14, containing the delivery device 16 and the proximal side 82 of the occlusion device 12, is withdrawn through the defect 74. Next, the catheter 14 is withdrawn further to expose the delivery device 16 and the proximal side 82 of the device 12. Thus, the proximal side 82 of the device 12 exits the catheter 14 and unfolds in the right atrium 62. Due to their shape memory, the arms of the proximal side 82 to expand against the septal wall 70 surrounding the defect 74 as the device 12 exits the catheter 14. Subsequently, the device 12 may be released from the delivery device 16.

However, as FIG. 5 depicts, the catheter 14, delivery device 16, or both, may distort tissue 84 at the defect 74. In FIG. 5, the upper portion of the defect 74 is distorted 84 by the insertion of the fairly stiff catheter 14. If the tissue at and around the treatment site is distorted 84, it is difficult for a physician to determine how the device 12 will actually seat once the device 12 is released, the catheter 14 and delivery device 16 are removed, and the tissue returns to its normal state. If the device 12 is not seated correctly, blood may continue to flow through the defect 74. In some instances, the device 12 may have to be retrieved and redeployed, which may require open heart surgery. These additional procedures increase cost and risk to the patient.

The present invention offers a way to reduce problems caused by the stiffness of the catheter 14 and delivery device 16. A tether is added to the system which allows a physician to determine whether the device is properly positioned prior to releasing the device. The tether is thin and extremely flexible, so it does not distort the surrounding tissue. In addition, the device is easily retrievable if it is not positioned properly because it has not been fully released. Rather, it remains connected to the tether as the position of the occlusion device is observed.

FIG. 6 is a more detailed view of the septal wall 70 and the defect 74 shown between the right atrium 62 and the left atrium 64 with the occlusion device 12 deployed across the defect 74. The delivery device 16 is attached to the coupler 18 and the coupler 18 is attached to the occlusion device 12. The catheter 14 has been slightly retracted. The septal wall 70 is no longer distorted but other portions of the heart may remain distorted by the stiff catheter 14 and delivery device 16.

FIG. 7 is a diagrammatic view of an occlusion device 12 which has been deployed and released from both the catheter 14 and delivery device 16 but remains connected to the tether 40 of the present invention. Shown, from left to right, is the catheter 14, the delivery device 16, the tether 40, the coupler 18, and the occlusion device 12 that has been fully deployed and is occluding the defect 74. The catheter 14 and delivery device 16 have been retracted. The occlusion device 12 is connected by the coupler 18 to the tether 40. Also shown are the right atrium 62, the left atrium 64, the right ventricle 66, the left ventricle 68, the atrial septal wall 70 and the ventricular septal wall 72.

Current delivery systems differ from the present invention in that they cannot retract the catheter 14 and delivery device 16 from the occlusion device 12 without fully releasing the device 12 from the system because they do not utilize a flexible tether 40. As such, these delivery systems must fully release the device 12 before the catheter 14 and delivery device 16 can be retracted. Therefore, the physician must evaluate the placement of the device 12 prior to release, and try to determine whether the device 12 is correctly placed and whether it will remain so after the catheter 14 and delivery device 16 are retracted. If the physician believes the device 12 is properly seated and will remain so, the device 12 is fully released. However, as the device 12 is released from the delivery device 16, any tension caused by the contortion of local tissue is also released. The release of tension may cause the device 12 to "jump" as it is released from the delivery device 16. Thus, the seating of the device 12 may shift as the tension is released.

After the device 12 is released, the patient undergoes a test to determine whether the defect has been sealed by the device 12. Physicians may use either ultrasound or X-Ray to determine whether blood continues to flow through the defect 74. If the device 12 was not properly seated or if it has shifted, the device 12 will not seal the defect 74. If blood continues to flow through the defect 74 the device 12 must be retrieved and redeployed.

FIG. 8 shows a diagrammatic view of a heart 60 with the occlusion device 12 deployed. The catheter 14 and delivery device 16 have been further retracted after the device 12 was deployed, leaving occlusion device 12 connected to the tether 40 by the coupler 18. By retracting the catheter 14 and the delivery device 16, the septum 70 is no longer distorted. The catheter 14 and delivery device 16 may be retracted further if necessary, until all tissue distortion is eliminated, while the tether 40 remains connected to the device 12. The tether 40 is thin and flexible and does not distort the heart 60, so the actual seating of the device 12 can be observed. In addition, because there is no contortion, there is no significant tension release that causes the device 12 to jump and possibly shift after release from the tether 40. Thus, the seating of the device should not change.

While the device 12 remains connected to the tether 40, a physician can perform tests (either ultrasound or X-Ray) to determine whether blood is shunting through the defect 74. The ability to determine whether the device 12 is seated properly before the device 12 is fully released eliminates the need to perform subsequent procedures resulting from poor seating. The device 12 can be retrieved easily if the seating is not good because the device 12 remains attached to the tether 40. To retrieve the device 12, the delivery device 16 is re-advanced over the tether 40 and reattached to the coupler 18. Once the delivery device 16 is reattached to the coupler 18, the delivery device 16 and coupler 18 are easily maneuverable; a physician can retrieve or redeploy the device 12 as needed.

If the device 12 is seated properly, however, the device 12 can be fully released. FIG. 9 shows a diagrammatic view of a heart 60 with the occlusion device 12 that has been fully released. The catheter 14 and delivery device 16 have been retracted and the coupler 18, along with the tether 40, have been detached from the occlusion device 12. In this embodiment, the proximal end of the tether 40 is twisted, by hand, to unscrew the coupler 18 from the occlusion device 12. When the coupler 18 and tether 40 are removed, the seating of the device 12 does not shift because there is no contortion or tension release that occurs when the coupler 18 and tether 40 are removed from the occlusion device 12. The seating of the device 12 should remain the same as it was when the ultrasound or X-Ray test was performed.

However, if the device 12 needs to be removed or redeployed, the physician can re-advance the delivery device 16 with the coupler attached 18 to the device 12 and reattach the coupler to the device 12. To retrieve the device 12, the coupler 18 is first reattached to the delivery device 16. Then, the delivery device 16, with the coupler 18 attached, is maneuvered to the occlusion device 12. Once the coupler 18 is properly positioned at the occlusion device 12, the coupler 18 can be screwed back into the occlusion device 12. The physician can then retrieve or redeploy the device 12 as needed. Alternatively, the device 12 may also be retrieved using standard procedures like a device.

Although the present invention has been described with reference to preferred embodiments, workers skilled in the art will recognize that changes may be made in form and detail without departing from the spirit and scope of the invention. For instance, a variety of attachment mechanisms could be used to attach the coupler to a delivery device and a medical device. Furthermore, though shown with an occluder, any medical device deployed through a catheter may benefit from this invention. Finally, the invention is not limited to use with the occluder shown. The invention may also include improvements disclosed in related applications and patents.

What is claimed is:

1. A medical system for delivering a medical device through a catheter, the system comprising:
    a hollow delivery device for positioning the medical device a via catheter;
    a flexible tether connected to the medical device and to the delivery device, wherein the tether is configured so that once the medical device is positioned by the delivery device, the tether can be detached from the delivery device while remaining connected to the medical device, and wherein the tether comprises a coupler having a first threaded end for threaded connection to the hollow delivery device and a second threaded end for threaded connection to the medical device.

2. The medical system of claim 1 wherein the tether is configured to detach from the medical device.

3. The medical system of claim 1 wherein the first and second threaded ends are threaded in opposite directions.

4. The medical system of claim 1 wherein the coupler is permanently fixed to the tether.

5. The medical system of claim 1 wherein the hollow delivery device comprises a threaded distal end for connection to the coupler.

6. The medical system of claim 2 wherein the medical device comprises a threaded end whereby it connects to the coupler.

7. The medical system of claim 1 wherein the tether is formed to have a variable diameter.

8. A delivery system for deploying an occlusion device, the delivery system comprising:
    a hollow delivery device having a threaded distal end;
    a coupler having a first threaded end for connection to the threaded distal end of the hollow delivery device and a second threaded end for connection to a occlusion device; and
    a tether connected to the coupler configured to extend through the hollow delivery device.

9. The delivery system of claim 8 wherein the first and second threaded ends are threaded in opposite directions.

10. The delivery system of claim 8 wherein the tether is formed to have a variable diameter.

11. The delivery system of claim 8 wherein the coupler is permanently fixed to the tether.

12. The delivery system of claim 8 wherein the occlusion device comprises a threaded center connection whereby it connects to the coupler.

13. A system for occluding a physical anomaly comprising:
    an occlusion device comprising:
        a first occluding body connected to a first support structure;
        a second occluding body connected to a second support structure; and
        a center connecting the first and second occluding bodies and having a threaded attachment site;
    a hollow delivery device having a threaded distal end;
    a guide catheter through which the occlusion device is delivered;
    a coupler having a first threaded end connected to the threaded distal end of the delivery device and a second threaded end connected to the threaded attachment site of the occlusion device; and
    a tether wire connected to the coupler and configured to extend through the hollow delivery device.

14. The system of claim 13 wherein the tether is formed to have a variable diameter.

15. The system of claim 13 wherein the first and second threaded ends are threaded in opposite directions.

16. The system of claim 13 wherein the coupler is permanently fixed to the tether.

* * * * *

UNITED STATES PATENT AND TRADEMARK OFFICE
CERTIFICATE OF CORRECTION

PATENT NO. : 6,913,614 B2
APPLICATION NO. : 10/431717
DATED : July 5, 2005
INVENTOR(S) : Joseph A. Marino et al.

It is certified that error appears in the above-identified patent and that said Letters Patent is hereby corrected as shown below:

Title Page # 57

Line 2 of the Abstract, delete "refract", insert --retract--

Column 2, Line 51, delete "can with drawn", insert --can be withdrawn--

Signed and Sealed this

Second Day of January, 2007

JON W. DUDAS
*Director of the United States Patent and Trademark Office*